United States Patent
DeHennis et al.

(10) Patent No.: US 10,016,133 B2
(45) Date of Patent: Jul. 10, 2018

(54) REMOTELY POWERED SENSOR WITH ANTENNA LOCATION INDEPENDENT OF SENSING SITE

(71) Applicant: Senseonics, Incorporated, Germantown, MD (US)

(72) Inventors: Andrew DeHennis, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 396 days.

(21) Appl. No.: 14/309,087

(22) Filed: Jun. 19, 2014

(65) Prior Publication Data

US 2014/0378791 A1    Dec. 25, 2014

Related U.S. Application Data

(60) Provisional application No. 61/836,721, filed on Jun. 19, 2013.

(51) Int. Cl.
*A61B 5/1455* (2006.01)
*A61B 5/00* (2006.01)
(Continued)

(52) U.S. Cl.
CPC .......... *A61B 5/0015* (2013.01); *A61B 5/0031* (2013.01); *A61B 5/1455* (2013.01);
(Continued)

(58) Field of Classification Search
None
See application file for complete search history.

(56) References Cited

U.S. PATENT DOCUMENTS 5,383,915 A * 1/1995 Adams ............... A61N 1/37282
                                                                128/903
5,517,313 A    5/1996 Colvin, Jr.
(Continued)

FOREIGN PATENT DOCUMENTS

WO   2006/127694 A2   11/2006
WO   2008/089282 A2   7/2008

*Primary Examiner* — Eric Winakur
*Assistant Examiner* — Marjan Fardanesh
(74) *Attorney, Agent, or Firm* — Rothwell, Figg, Ernst & Manbeck, P.C.

(57) ABSTRACT

A system and method for detecting the amount or concentration of an analyte in a medium in living organism. The system may include an analyte sensor module and a transmitter module, which may be separate and distinct components. The analyte sensor module and transmitter module may be at different locations but connected by one or more transmission elements. The analyte sensor may include indicator elements configured to exhibit a detectable property based on the amount or concentration of the analyte in proximity to the indicator elements. The analyte sensor may include sensor elements configured to generate a data signal based on the detectable property exhibited by the indicator elements. The transmission elements may be configured to convey data signals generated by the sensor elements from the analyte sensor module to the transmitter module. The transmitter module may include an antenna.

10 Claims, 5 Drawing Sheets

(51) Int. Cl.
A61B 5/1459 (2006.01)
A61B 5/145 (2006.01)

(52) U.S. Cl.
CPC ........ A61B 5/1459 (2013.01); A61B 5/14532 (2013.01); *A61B 2560/0219* (2013.01); *A61B 2562/162* (2013.01)

(56) References Cited

U.S. PATENT DOCUMENTS

| | | |
|---|---|---|
| 6,330,464 B1 | 12/2001 | Colvin, Jr. et al. |
| 6,400,974 B1 | 6/2002 | Lesho |
| 2006/0049957 A1* | 3/2006 | Surgenor ........... A61B 5/04001 340/4.1 |
| 2007/0156205 A1 | 7/2007 | Larson et al. |
| 2010/0073669 A1* | 3/2010 | Colvin, Jr. ................ G01J 3/02 356/218 |
| 2010/0280568 A1 | 11/2010 | Bulkes et al. |
| 2013/0211213 A1 | 8/2013 | DeHennis et al. |

\* cited by examiner

REMOTELY POWERED SENSOR WITH ANTENNA LOCATION INDEPENDENT OF SENSING SITE

CROSS-REFERENCE TO RELATED APPLICATIONS

The present application claims the benefit of priority to U.S. Provisional Application Ser. No. 61/836,721, filed on Jun. 19, 2013, which is incorporated herein by reference in its entirety.

FIELD OF THE INVENTION

This invention relates to a system and method for detecting the presence or concentration of an analyte in a liquid or gaseous medium, such as, for example, the human body. More particularly, the invention relates to a system comprising an analyte sensor module and a power and signal transmitter module that are separate and distinct components but are connected by a wire or cable whereby the analyte sensor module can be implanted within an organism at a locus that is ideal for sensing an analyte of interest and the power and signal transmitter module can be implanted within the organism at a location that is ideal for communication with a reader/transmission module that is external to the organism.

BACKGROUND OF INVENTION

U.S. Pat. No. 5,517,313, the disclosure of which is incorporated herein by reference, describes a fluorescence sensing device comprising a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, such that incident light from the light source causes the indicator elements to fluoresce. The high-pass filter allows emitted light to reach the photodetector, while filtering out scattered incident light from the light source. An analyte is allowed to permeate the fluorescent matrix, changing the fluorescent properties of the indicator material in proportion to the amount of analyte present. The fluorescent emission is then detected and measured by the photodetector, thus providing a measure of the amount or concentration of analyte present within the environment of interest.

One advantageous application of a sensor device of the type disclosed in U.S. Pat. No. 5,517,313 is to implant the device in the body of an organism (e.g., a human or animal), either subcutaneously or intravenously or otherwise, to allow instantaneous measurements of analytes to be taken at any desired time. For example, it is desirable to measure the concentration of oxygen in the blood of patients under anesthesia, or of glucose in the blood of diabetic patients.

Variations and improvements on the sensing device described in U.S. Pat. No. 5,517,313 are described in U.S. Pat. Nos. 6,330,464 and 6,400,974, as well as in United States Patent Application Publication No. 2013/0211213, the respective disclosures of which are hereby incorporated by reference in their entireties.

Existing sensor systems, including sensors and systems described in the disclosures referenced above, comprise a 'grain of rice' sized sensor configured to be implanted in vivo subcutaneously and that includes all of the functional electronics needed to enable implantable sensing of glucose or other analyte of interest. These functional electronics include the sensing element(s), such as light sources(s) (e.g., LED), filter(s) and photosensor(s), the optical interface, the circuitry that generates signals having strength and/or other characteristics that are dependent on the strength and/or other detectable characteristics of the optical radiation detected by the sensing elements, the integrated circuit functionality to wirelessly communicate the signals and receive commands, and an antenna that is inductively coupled to an antenna of a reader/transmitter that is external to the organism in which the sensor is implanted. Such a sensor configuration is well-suited for insertion of the sensor element in an interstitial space and communication with a reader/transmitter that is worn outside the skin, but in close to proximity to the implanted sensor element.

This close proximity between the implanted sensor element and the external reader/transmitter does provide good telemetry coupling between the sensor element and the external reader/transmitter as well as access to glucose (or other analyte) concentration in the interstitial fluid.

A shortcoming that exists with the state of the art, however, is that the system as described above is dependent on having within the sensor element an antenna that can receive power and commands from an external reader/transmitter, as well as sensing the presence of analyte at the same location at which the sensor element is implanted. Such dual requirements sometimes conflict with each other and can limit the range of applications in which this sensor system can be used to detect analytes in vivo and wirelessly communicate with an external device.

SUMMARY OF THE INVENTION

A system embodying aspects of the invention solves the sometimes conflicting requirements of having an analyte to be sensed in proximity to the sensor implant locus and a reasonable wireless transmission distance between the implanted sensor element and the external reader/transmitter by physically and electrically partitioning the analyte-sensing and power/signal transmitting components of the implanted sensor element and connecting them with a wire or cable. Thus, the portion of the sensor housing the analyte-sensing components can be implanted in a part of the body that is most ideal for detecting a particular analyte of interest, the portion of the sensor housing the power/signal transmitting components can be implanted in a location that is most preferable for transmission with an external reader/transmitter, and the two implanted portions of the sensor can exchange power and data signals via the wire or cable connecting them, which itself may be implanted within the organism.

One aspect of the present invention provides a system for detecting an amount or concentration of an analyte in vivo within a living organism. The system may include an analyte sensor module and a transmitter module. The analyte sensor module may be configured to be implanted, in vivo, within the living organism. The analyte sensor may comprise indicator elements configured to exhibit a detectable property based on the amount or concentration of the analyte in proximity to the indicator elements. The sensor elements may be configured to generate a data signal based on the detectable property exhibited by the indicator elements. The transmitter module may be configured to be implanted subcutaneously within the living organism at a different location than the analyte sensor module. The transmitter module may be tethered to the analyte sensor module by one or more transmission elements. The transmission elements may be configured to convey data signals generated by the sensor elements from the analyte sensor module to the transmitter module. The transmitter module may include an antenna configured for conveying radio frequency signals.

Other features and characteristics of the present invention, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures

BRIEF DESCRIPTION OF THE DRAWINGS

The accompanying drawings, which are incorporated herein and form part of the specification, illustrate various, non-limiting embodiments of the present invention. In the drawings, common reference numbers indicate identical or functionally similar elements.

DETAILED DESCRIPTION OF THE INVENTION

Figure 1:
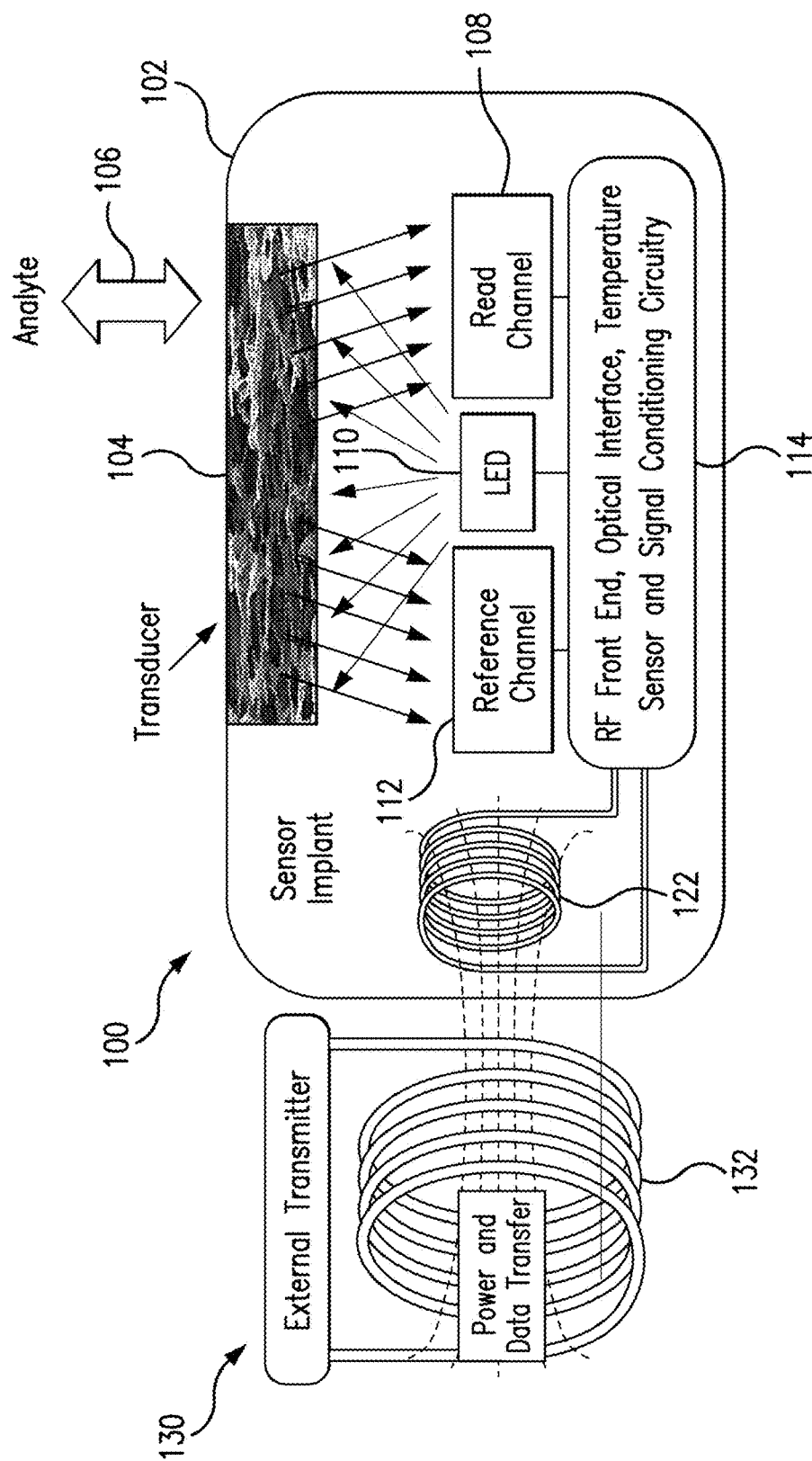
FIG. 1 is a schematic view of a known implantable sensor and external reader/transmitter.

Unless defined otherwise, all terms of art, notations and other scientific terms or terminology used herein have the same meaning as is commonly understood by one of ordinary skill in the art to which this disclosure belongs. All patents, applications, published applications, and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, inside, outside, inner, outer, proximal, distal, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

FIG. 1 is a schematic view of a known sensor system including an implantable sensor 100 and an external reader module 130. The implantable sensor 100 includes an antenna 122 configured to convey and receive radio frequency signals, a light source 110, indicator elements 104 responsive to an analyte 106 in proximity to and/or in contact with the indicator elements 104, one or more photosensors 108 of a read channel and one or more reference photosensors 112 of a reference channel. The photosensors 108, 112 may be photodiodes, phototransistors, photo resistors or other photosensitive elements, as disclosed in U.S. Pat. No. 7,822,450, the disclosure of which is hereby incorporated by reference. In some embodiments, the reference photosensors 112 may be omitted. The sensor 100 may further include other components, such as, a radio frequency processing components, an optical interface, a temperature sensor, and signal conditioning circuitry, as generally indicated at box 114. All components of the sensor 100 may be encapsulated within a housing 102. External reader module 130, which may be incorporated into an implement worn on a person's body, such as, for example, an armband or wrist-watch type bracelet (not shown), includes an antenna 132 configured to convey and receive radio frequency signals.

The implantable sensor 100 receives power and data from the reader module 130 through the antenna 122, which may be, for example, a coil. The sensor antenna 122 may receive power from the reader antenna 132, e.g., through inductive coupling. The power received by the sensor antenna 122 drives the light source 110, which may be, for example, a light emitting diode (LED) or, possibly, an ultra-violet light emitting diode. The light source 110 emits radiation, including radiation over a wavelength that interacts with the indicator elements 104. The indicator elements 104 may be fluorescent indicator molecules or absorption molecules that indicate the presence of an analyte by changes in the fluorescence or absorption of the indicator elements 104 that are indicative of the amount or concentration of a particular analyte.

The photosensor(s) 108 of the read channel is (are) sensitive to fluorescent light of a particular wavelength emitted by the indicator elements 104, such that, in combination with the components of box 114, a data signal is generated by the read channel 108 in response thereto that is indicative of the level of fluorescence of the indicator elements and, thus, the amount or concentration of analyte of interest, such as glucose. The photosensor(s) 112 of the reference channel is(are) sensitive to light of a particular wavelength emitted by the light source 110. To reduce optical cross-talk, or noise, the signal generated by the read channel 108 can be adjusted based on the signal generated by the reference channel 112 to remove portions of the signal generated by the read channel 108 that are due to light from the light source 110 or other ambient light.

The antenna 122 communicates a data signal corresponding to the amount or concentration of analyte, as determined by the signal detected by photosensors 108, to the reader module 130 via the antenna 132. In one non-limiting example, information may be communicated between the sensor 100 and the reader module 130 as described in U.S. Pat. No. 7,553,280, the disclosure of which is incorporated herein by reference in its entirety.

The sensor antenna 122 and reader antenna 132 may be coils. The reader antenna 132 may generate an electromagnetic wave or electrodynamic field to induce a current in the sensor antenna 122. The reader antenna 132 may also convey command signals to the sensor 100, for example, by modulating the electromagnetic field used to power the sensor 100. Moreover, the reader antenna 132 may receive data signals from the sensor 100, for example, by detecting modulations in the electromagnetic field generated by the sensor antenna 122.

Further details of the specific components of an implantable sensor are described in previously referenced U.S. Pat. Nos. 6,330,464, 7,553,280 and 6,400,974, as well as in United States Patent Application Publication No. 2013/0211213, all of which are incorporated by reference herein in their entireties.

Figure 2:
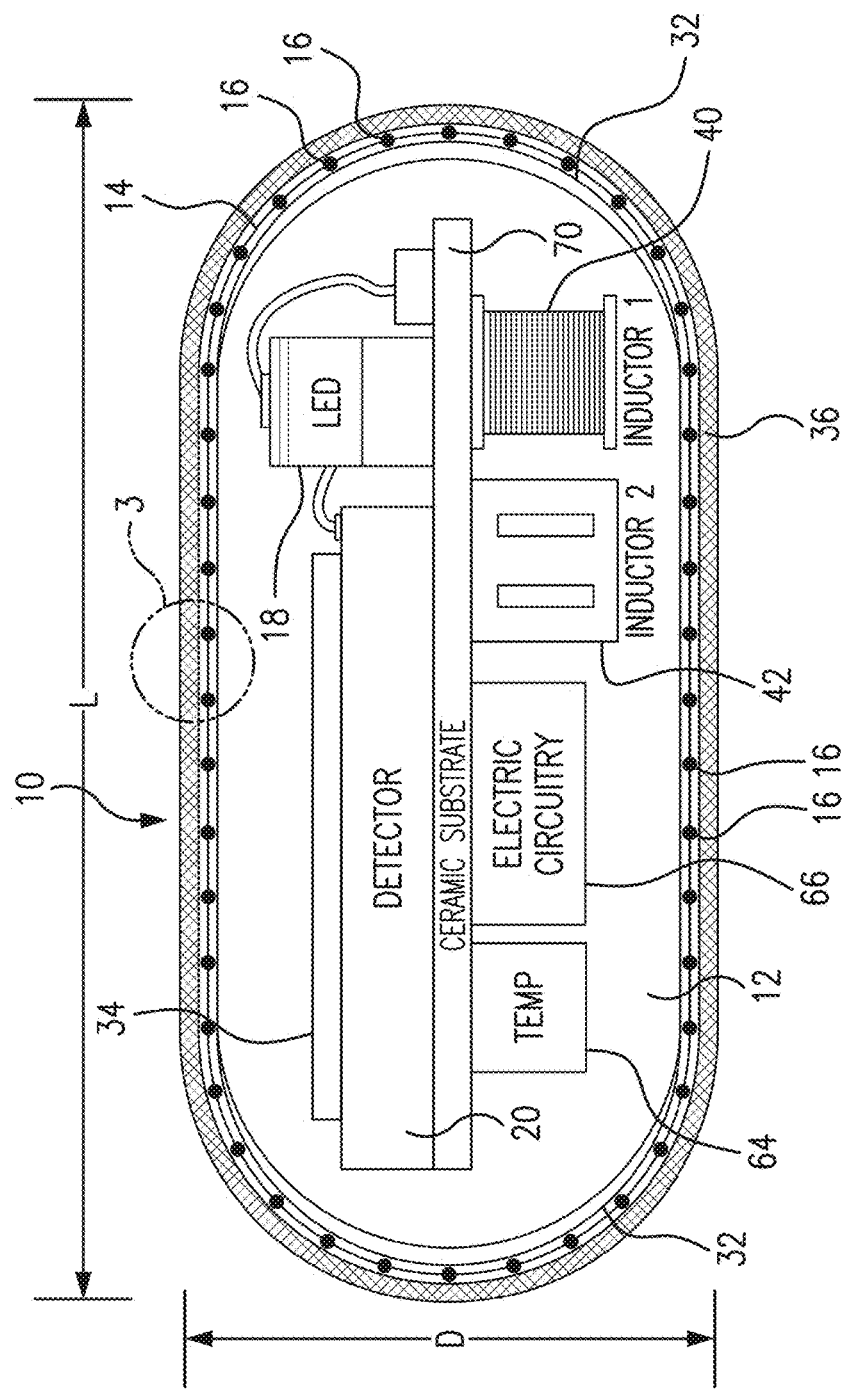
FIG. 2 is a schematic view of a known implantable sensor

By way of example, further details of a known optical-based sensor 10 are shown in FIG. 2. The sensor 10 has as its primary components a sensor body 12; a matrix layer 14 (i.e., polymer graft) coated over the exterior surface of the sensor body 12, with fluorescent indicator elements 16 distributed throughout the layer; a radiation source 18, e.g. an LED, that emits radiation, including radiation over a range of wavelengths that interact with the indicator elements (referred to herein simply as "radiation at a wavelength that interacts with the indicator elements"), i.e., in the case of a fluorescence-based sensor, a wavelength which causes the indicator elements 16 to fluoresce; and a detector 20, e.g., a photosensitive element or photosensor, which, in the case of a fluorescence-based sensor, is sensitive to fluorescent light emitted by the indicator elements 16 such that a signal is generated in response thereto that is indicative of the level of fluorescence emitted by the indicator elements. In the simplest embodiments, indicator elements 16 could simply be coated on the surface of the sensor body 12. In preferred embodiments, however, the indicator elements 16 are contained within the matrix layer 14, which comprises a biocompatible polymer matrix that is prepared according to methods known in the art and coated on the surface of the sensor body as described in previously-incorporated U.S. Pat. No. 6,330,464. Suitable biocompatible matrix materials, which must be permeable to the analyte, include methacrylates and hydrogels which, advantageously, can be made selectively permeable—particularly to the analyte—e.g., they perform a molecular weight cut-off function.

The sensor body 12 advantageously is formed from a suitable, optically transmissive polymer material which has a refractive index sufficiently different from that of the medium in which the sensor 10 will be used such that the polymer will act as an optical wave guide. Preferred materials include acrylic polymers such as polymethylmethacrylate, polyhydroxypropylmethacrylate and the like, and polycarbonates, such as those sold under the trademark Lexan®. The material allows radiation employed by the device— radiation generated by the radiation source 18 (e.g., light at an appropriate wavelength in embodiments in which the radiation source is an LED) and, in the case of a fluorescence-based embodiment, fluorescent light emitted by the indicator elements 16—to travel through it. Radiation (e.g., light) is emitted by the radiation source 18 and (at least some) is reflected internally at the surface of the sensor body 12 thereby "bouncing" back-and-forth throughout the interior of the sensor body 12.

As further illustrated in FIG. 2, the sensor 10 may also include reflective coatings 32 formed on the ends of the sensor body 12, between the exterior surface of the sensor body and the matrix layer 14, to maximize or enhance the internal reflection of the radiation and/or light emitted by fluorescent indicator elements 16. The reflective coatings 32 may be formed, for example, from paint or from a metallized material (provided such metallized material does not impede transmission of telemetry signals to and from the sensor, described below).

As still further illustrated in FIG. 2, an optical filter 34 may be provided on the light-sensitive surface of the photosensitive element (photosensor) 20. This filter prevents or substantially reduces the amount of radiation generated by the source 18 from impinging on the photosensitive surface of the photosensitive element 20. At the same time, the filter 34 allows fluorescent light emitted by fluorescent indicator elements 16 to pass through it to strike the photosensitive region of the detector 20. This significantly reduces "noise" in the photosensor signal that is attributable to incident radiation from the source 18.

An application for which the sensor 10 is suitable—although by no means the only application for which it is suitable—is measuring various biological analytes in the human body, e.g., glucose, oxygen, toxins, pharmaceuticals or other drugs, hormones, and other metabolic analytes. The specific composition of the matrix layer 14 and the indicator elements 16 may vary depending on the particular analyte the sensor is to be used to detect and/or where the sensor is to be used to detect the analyte (i.e., in the blood or in subcutaneous tissues). Two constant requirements, however, are that the matrix layer 14 facilitate exposure of the indicator elements 16 to the analyte and that the optical characteristics of the indicator elements 16 (e.g., the level of fluorescence of fluorescent indicator elements) are a function of the amount or concentration of the specific analyte to which the indicator elements are exposed.

To facilitate use in-situ in the human body, the sensor 10 is formed in a smooth, oblong or rounded shape. Advantageously, it has the approximate size and shape of a bean or a pharmaceutical gelatin capsule, i.e., it is on the order of approximately 500 microns to approximately 0.5 inch in length L and on the order of approximately 300 microns to approximately 0.3 inch in diameter D, with generally smooth, rounded surfaces throughout. This configuration permits the sensor 10 to be implanted into the human body, i.e., dermally or into underlying tissues (including into organs or blood vessels) without the sensor interfering with essential bodily functions or causing excessive pain or discomfort.

The sensor 10 shown in FIG. 2 is wholly self-contained. In other words, in specific embodiments, the sensor 10 may be constructed in such a way that no electrical leads extend into or out of the sensor body to supply power to the sensor (e.g., for driving the source 18) or to convey signals from the sensor. Rather, sensor 10 may include a power source 40 that is wholly embedded or encapsulated within the sensor body 12 and a data communication element 42 that also is entirely embedded or encapsulated within the sensor body 12.

Figure 3:
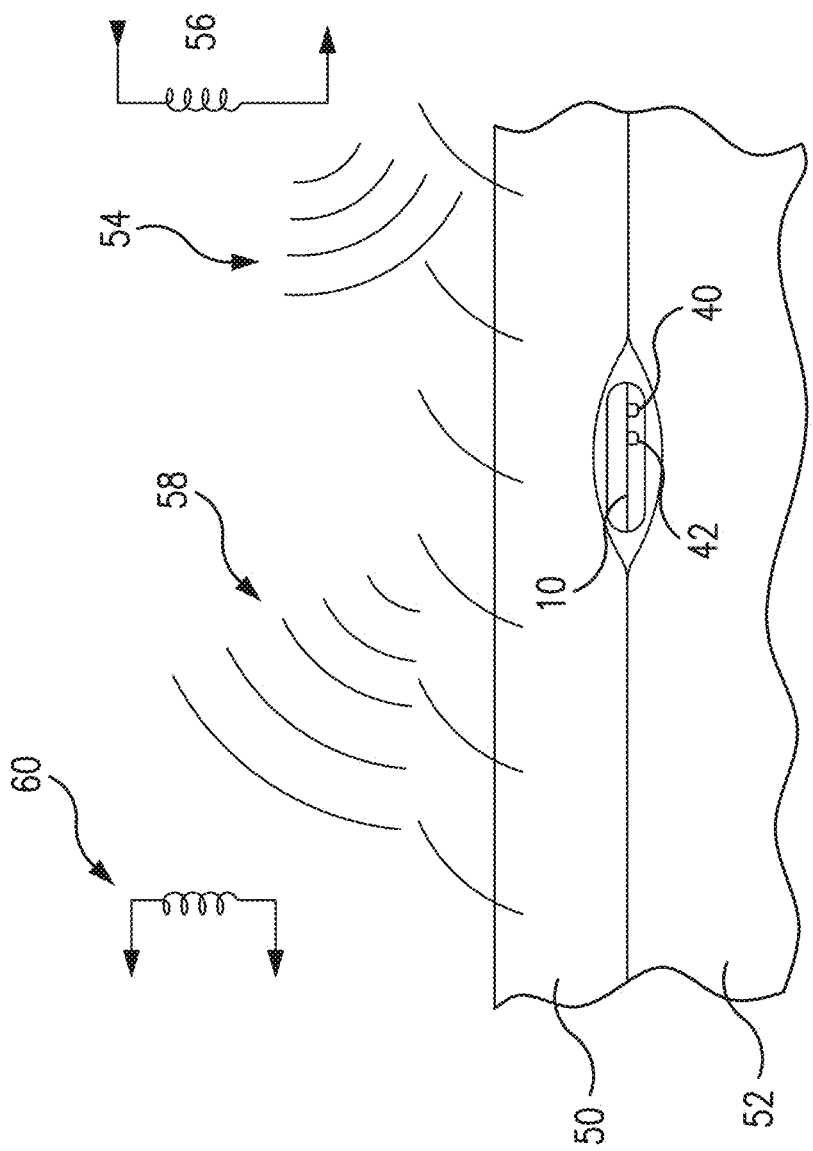
FIG. 3 is a schematic view demonstrating use of the implantable sensor and external reader module.

In one embodiment, the power source 40 is an inductor, as is the data communication element 42. Thus, when the sensor 10 is implanted in the body, e.g. between the skin 50 and subcutaneous tissues 52 as shown in FIG. 3, the sensor can be powered—i.e., the radiation source can be caused to emit radiation which interacts with the indicator elements 16—by exposing the sensor to a field of electromagnetic radiation 54 created, for example, by an inductor coil 56 that is housed in an external reader module (not shown) positioned near the sensor. Similarly, the data communication element 42, as an inductor, generates an electromagnetic field 58 that is indicative of the level of light striking the photosensitive element 20 and hence the presence or concentration of analyte. The field 58 constitutes a signal that can be detected by an external receiver 60 which may also be incorporated into the external reader module. The signal may be, for example, a 50 megahertz carrier, amplitude modulated signal, a frequency modulated signal, a digital signal, or any other type of electromagnetic wave signal that would be known to one having skill in the art.

In preferred embodiments a single coil and a single inductor are for all telemetry. In such an embodiment, the coil 56 generates the electromagnetic wave 54 at one frequency to induce a current in the inductor 40, which powers the source of radiation 18; the amount of internally reflected light sensed by the photosensitive element 20 is conveyed by the same inductor 40 as a modulated electromagnetic wave which induces a current in coil 56. This modulated wave is generated by modulating the current flowing through inductor 40 by the photosensitive element 20 as a function of detected light and is detected by measuring the resulting induced current in coil 56.

Other telemetry schemes that may be employed between an external reader module and an implantable sensor are described in previously-referenced U.S. Pat. Nos. 6,330,464, 7,553,280 and 6,400,974, as well as in United States Patent Application Publication No. 2013/0211213.

With respect to the other components shown in FIG. 2, a temperature sensor 64 and an optional signal amplifier, which is part of the electric circuitry 66, may also advantageously provided. The temperature sensor 64 measures the locally surrounding temperature of the ambient tissues and the indicator molecule environment and provides this information to the control logic circuit (not shown). The control logic circuit correlates fluorescence level, for example, with analyte concentration level, thereby correcting the output signal for variations affected by temperature. Amplifier 66 is a relatively simple gain circuit which amplifies the signal generated by the photodetector 20.

Although the embodiment of a sensor 10 shown in FIG. 2 has a single radiation source 18 (LED) and photosensitive element 20 (photosensor), thereby permitting detection of a single analyte, other configurations and components are possible. For example, two or more different types of indicator elements may be provided to sense the presence or concentration of two or more analytes, respectively, with two or more photosensitive elements being provided on the ceramic substrate 70. Each photosensitive element may have its own filter 34 designed to allow light from the respective indicator elements to pass through to it. Similarly, a "two-channel" embodiment could be developed to measure analyte concentration by two different sensing schemes. In one such embodiment, for example, some of the indicator elements would be fluorescent indicator molecules and the rest of the indicator elements would be radiation-absorbing indicator molecules (as described in previously-incorporated U.S. Pat. No. 6,330,464). Two separate photosensitive elements would be provided, each with its own appropriate filter—one to measure fluorescent light emitted by the fluorescent indicator elements and one to measure radiation generated by the source and reflected throughout the sensor, with some absorption by the radiation-absorbing indicator molecules. Additionally, other types of photosensitive elements may be used, e.g., photoresistors, phototransistors, photodiodes, photodarlingtons, photovoltaic cells, positive insulating negative photodiodes, large-area photodiodes, avalanche photodiodes, charge coupled devices, etc.

Moreover, although sensor 10 has been described above primarily as functioning based on fluorescence of indicator elements, the sensor may operate based on the light-absorbing characteristics of light-absorbing indicator elements. Such a sensor according is described in U.S. Pat. No. 5,517,313, referenced above, and preferably employs a bean- or pharmaceutical gelatin capsule construct as described above.

Figure 4:
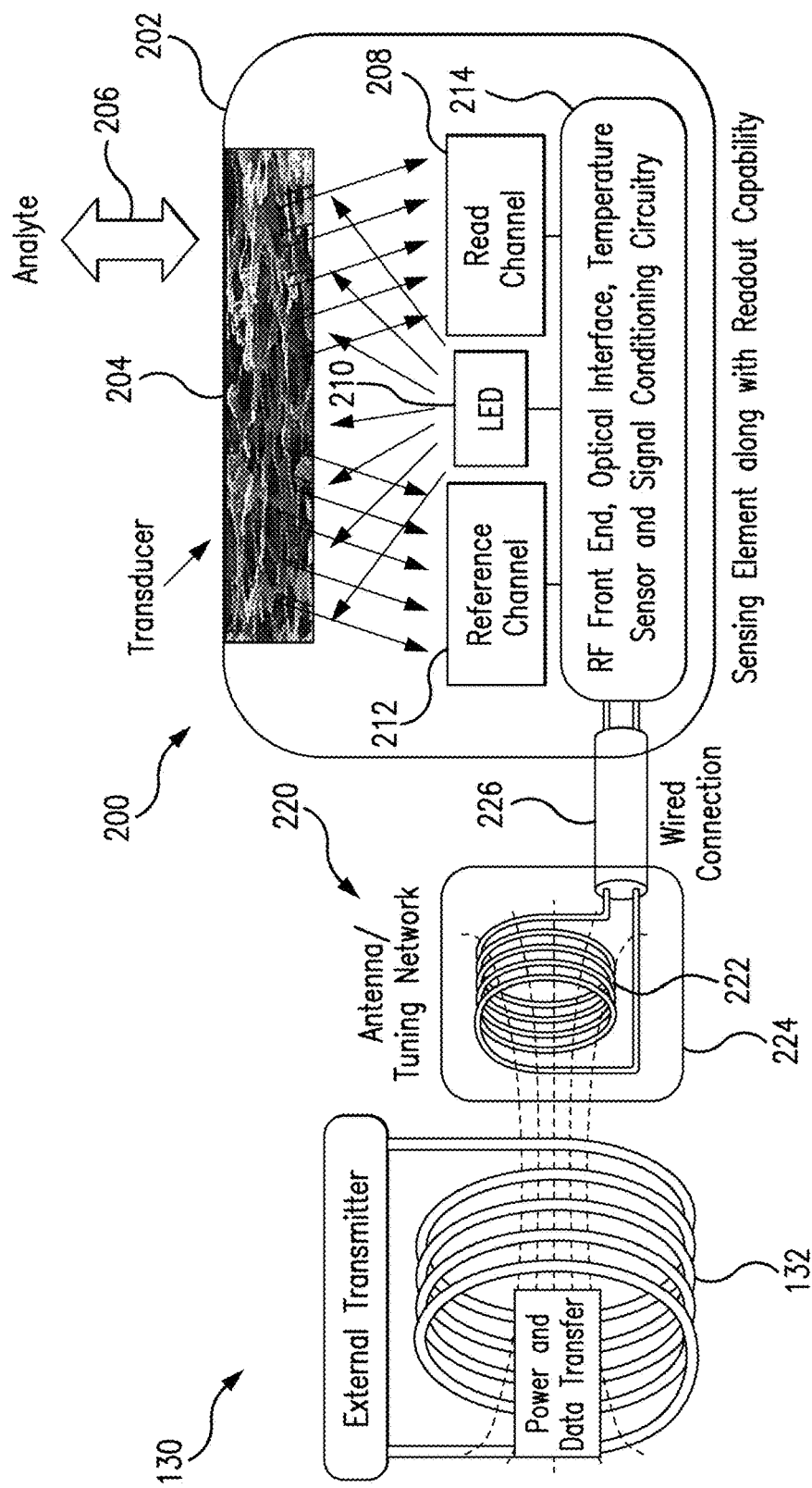
FIG. 4 is a schematic view of an implantable analyte sensor module, a transmitter module tethered to the analyte sensor module, and an external reader module.

As opposed to the wholly self-contained sensor shown in FIGS. 1-3, in a sensor system embodying aspects of the present invention, the analyte-sensing functionality and the signal/power generation and transmission functionality of the sensor may be separated into distinct, but connected modules, as shown in FIG. 4.

FIG. 4 is a schematic view of a sensor system embodying aspects of the present invention. In some embodiments, the sensor system may include an implantable analyte sensor module 200, an implantable transmitter module 220, and an external reader module 130. The analyte sensor module 200 may include a light source 210, indicator elements 204 responsive to an analyte 206 in proximity to and/or in contact with the indicator elements 204, one or more photosensors 208 of a read channel and one or more reference photosensors 212 of a reference channel. The photosensors 208, 212 may be photodiodes, phototransistors, photo resistors or other photosensitive elements, as disclosed in previously-incorporated U.S. Pat. No. 7,822,450. In some embodiments, the reference photosensors 212 may be omitted. The analyte sensor module 200 may further include other components 214, such as, for example, one or more of a radio frequency processing components, optical interface, temperature sensor, and signal conditioning circuitry. For example, in one non-limiting embodiment, components 214 may include one or more of the input/output (I/O) circuit, measurement controller, and analog interface described with reference to FIGS. 5 and 6 of U.S. Patent Application Publication No. 2013/0211213, which is incorporated herein by reference in its entirety. In some embodiments, the components of the analyte sensor module 200 may be encapsulated within a housing 202.

In some embodiments, the photosensor(s) 208 of the read channel may be sensitive to fluorescent light emitted by the indicator elements 204, such that, in combination with the components 214, a data signal is generated by the read channel 208 in response thereto that is indicative of the level of fluorescence of the indicator elements 204 and, thus, the amount or concentration of analyte of interest, such as, for example, glucose. The photosensor(s) 212 of the reference channel may be sensitive to light of a particular wavelength emitted by the light source 110. As explained above, in some embodiments, to reduce optical cross-talk, or noise, the signal generated by the read channel 208 can be adjusted based on the signal generated by the reference channel 212 to remove portions of the signal generated by the read channel 208 that are due to light from the light source 210 or other ambient light.

Further details regarding the components, construction, assembly, and functionality of the analyte sensor module 200 can be derived from the description above of sensor 10 shown in FIG. 2 as well as from previously-referenced U.S. Pat. Nos. 6,330,464 and 6,400,974 and United States Patent Application Publication No. 2013/0211213.

In some embodiments, the transmitter module 220 may include an antenna 222 encapsulated within a housing 224 and configured to convey and receive radio frequency signals. The transmitter module 220 may be tethered, e.g., electrically connected, to the analyte sensor module 200 by one or more transmission elements 226, which may comprise, for example, insulated electrical transmission wires and/or coaxial cable.

As with the self-contained sensor 100 shown in FIG. 1, in some embodiments, an external reader module 130 that may be used in conjunction with the analyte sensor module 200 and the transmitter module 220 of FIG. 4, may be incorporated into an implement worn on a person's body, such as, for example, a wrist-watch type bracelet (not shown) and includes an antenna 132 configured to convey and receive radio frequency signals. In other embodiments, the external reader module 130 may be incorporated into a smartphone, smart watch, computer (hand held or otherwise), tablet (e.g. an ipad), or other portable implement such as, for example, a fitbit. In still other embodiments, the external reader module 130 used in conjunction with the analyte sensor module 200 may communicate (e.g., via wireless or wired communication) with display device (e.g., smartphone, smart watch, computer, tablet, or other portable implement).

In some embodiments, the transmission module 220 may receive power and data from the reader module 130 through the antenna 222, which may be, for example, a coil. The antenna 222 may receive power from the reader antenna 132, e.g., through inductive coupling. The power received by the antenna 222 of the transmitter module is transmitted by the transmission element 226 to the analyte sensor module 200 to drive the light source 210, which may be, for example, a light emitting diode (LED) or, possibly, an ultra-violet light emitting diode. The light source 210 emits radiation, including radiation over a wavelength that interacts with the indicator elements 204. The indicator elements 204 may be fluorescent indicator molecules or absorption molecules that indicate the presence of an analyte by detectable changes in the fluorescence or absorption of the indicator elements 204 that are indicative of the amount or concentration of a particular analyte. In some embodiments, the light source 210 may additionally or alternatively be driven with power from one or more internal power sources, such as, for example, a battery, which may be included in the analyte sensor module 200 or transmitter module 220.

In some embodiments, the data signal generated by read channel 208 (possibly adjusted based on output of the reference channel 212) of the analyte sensor module 200 may be transmitted by the transmission elements 226 to the transmitter module 220. The antenna 222 of the transmitter module 220 may communicate a data signal, which may correspond to the amount or concentration of analyte in proximity to the indicator elements 204, as determined by the signal detected by photo sensors 208, to the reader module 130 via the antenna 132.

In some embodiments, as in the self-contained sensor 100 of FIG. 1, the antenna 222 of the transmitter module 220 and reader antenna 132 may be coils. The reader antenna 132 may generate an electromagnetic wave or electrodynamic field to induce a current in the antenna 222 that is transmitted by the transmission elements 226 to the analyte sensor module 200. The reader antenna 132 may also convey command signals to antenna 222 of the transmitter module 220 that are conveyed to the analyte sensor module 200 via transmission elements 226, such as commands for modulating the electromagnetic field used to power the sensor module 200. Moreover, the reader antenna 132 may receive data signals from the transmitter module 220, for example, by detecting modulations in the electromagnetic field generated by the antenna 222 of the transmitter module.

Further details regarding the telemetry between the external reader module 130 and the transmitter module 22 can be derived from the description above of sensor 10 shown in FIG. 2 as well as from previously-referenced U.S. Pat. Nos. 6,330,464, 7,553,280 and 6,400,974 and United States Patent Application Publication No. 2013/0211213, each incorporated herein by reference.

In the embodiment illustrated in FIG. 4, the components 214 are encapsulated within the housing 202 of the analyte sensor module 200. However, this is not required, and, in some alternative embodiments, one or more of the components 214 (e.g., radio frequency processing components and/or the signal conditioning circuitry) may be encapsulated within the housing 224 of the transmitter module 220. For example, in one non-limiting embodiment having the input/output (I/O) circuit, measurement controller, and analog interface described with reference to FIGS. 5 and 6 of U.S. Patent Application Publication No. 2013/0211213, the analog interface may be encapsulated within the housing 202 of the analyte sensor module 200 while the I/O circuit and measurement controller may be encapsulated within the housing 224 of the transmitter module 220.

Figure 5:
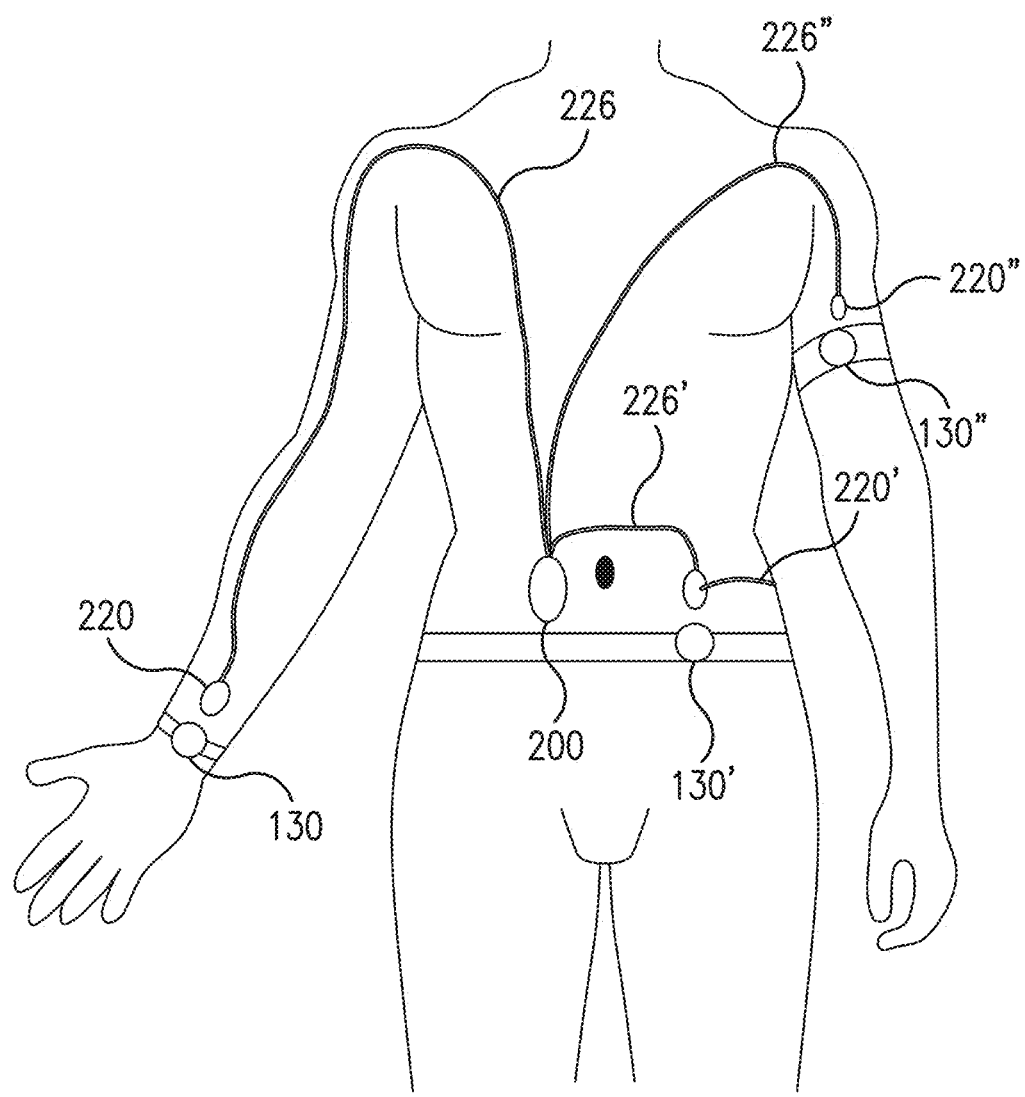
FIG. 5 is a schematic view of an implantable analyte sensor module, a transmitter module tethered to the analyte sensor module, and an external reader module with the sensor module and the transmitter module implanted into a human being and the external reader module being worn on the human.

FIG. 5 shows exemplary implementations of embodiments of the invention. In a first implementation, the analyte sensor module 200 is implanted within the abdominal area of the person, e.g., in the intra-peritoneal space at a location that is ideal for detecting certain analytes, such as, for example, glucose. (It should be noted that FIG. 5 is not drawn to scale; the analyte sensor module 200 would typically be much small than is shown in FIG. 5.) The intra-peritoneal space, however, is relatively deep within the body, and thus that location of the analyte sensor module 200 would not be ideal for wireless telemetry between the module 200 and an external reader module. Thus, in one non-limiting embodiment, a transmitter module 220, connected to the analyte sensor module 200 by transmission element 226, is implanted subcutaneously in the person's arm (e.g., at or near the wrist) where an external reader module 130 carried, for example, on a wrist-watch type bracelet worn on the person's wrist is able to effectively exchange radio signals with the transmitter module 220. Thus, the sensor system is able to detect and monitor analytes in the remote location of the analyte sensor module 200, e.g., in the intra-peritoneal space.

In an alternative non-limiting embodiment also shown in FIG. 5, a transmitter module 220', connected to the analyte sensor module 200 by transmission element 226', is implanted subcutaneously in the person's abdomen where an external reader module 130' carried on a belt worn around the person's waist is able to effectively exchange radio signals with the transmitter module 220'.

In another alternative non-limiting embodiment, which is also shown in FIG. 5, a transmitter module 220", connected to the analyte sensor module 200 by transmission element 226", is implanted subcutaneously in the person's abdomen where an external reader module 130" carried on an armband worn around the person's arm is able to effectively exchange radio signals with the transmitter module 220". The transmission elements 226, 226', and 226" may be, for example, insulated electrical transmission wires, coaxial cable, and/or any suitable means of transmitting data and/or power.

While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the present invention is deemed to include all modifications and variations encompassed within the spirit and scope of the following appended claims.

The invention claimed is:

1. A system for detecting an amount or concentration of an analyte in vivo within a living organism, said system comprising:

A. an analyte sensor module configured to be implanted, in vivo, within the living organism and comprising:
   (A1) indicator elements configured to exhibit a detectable property based on the amount or concentration of the analyte in proximity to the indicator elements;
   (A2) sensor elements configured to generate a data signal based on the detectable property exhibited by said indicator elements; and
   (A3) a sensor housing encapsulating one or more of the sensor elements;
B. a transmitter module configured to be implanted subcutaneously within the living organism at a different location than said analyte sensor module, said transmitter module comprising:
   (B1) an antenna configured for conveying radio frequency signals; and
   (B2) a transmitter housing encapsulating the antenna, wherein the transmitter housing is separate from the sensor housing; and
C. one or more transmission elements that tether said transmitter module to said analyte sensor module and are configured to convey data signals generated by said sensor elements from said analyte sensor module to said transmitter module.

2. The system of claim 1, further comprising an external reader module including an antenna configured for inductive coupling with said antenna of said transmitter module, said external reader module being configured to receive data signals conveyed by said transmitter module via the inductive coupling.

3. The system of claim 2, wherein the external reader module is configured to convey a power signal to said transmitter module via the inductive coupling to generate power within said transmitter module.

4. The system of claim 1, wherein said sensor elements comprise at least one light source and one or more photosensors configured to sense an optical emission from said indicator elements.

5. The system of claim 1, wherein said transmission elements comprise at least one of a wire and a coaxial cable.

6. The system of claim 1, wherein said antenna of said transmitter module comprises an inductive coil.

7. The system of claim 1, wherein the one or more transmission elements are configured to transmit power from said transmitter module to said analyte sensor module for powering said sensor elements, and the antenna is configured for receiving and conveying radio frequency signals.

8. The system of claim 1, wherein the transmitter module further comprises one or more electronic components, and the transmitter housing encapsulates the one or more electronic components.

9. The system of claim 1, wherein at least a portion of the one or more transmission elements is not encapsulated within the sensor housing, and at least a portion of the one or more transmission elements is not encapsulated within the transmitter housing.

10. The system of claim 1, wherein the analyte sensor module further comprises one or more electronic components, and the sensor housing encapsulates the one or more electronic components.

* * * * *

UNITED STATES PATENT AND TRADEMARK OFFICE
CERTIFICATE OF CORRECTION

PATENT NO.         : 10,016,133 B2
APPLICATION NO.    : 14/309087
DATED              : July 10, 2018
INVENTOR(S)        : DeHennis et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 488 days.

Signed and Sealed this
Ninth Day of July, 2019

Andrei Iancu
*Director of the United States Patent and Trademark Office*